United States Patent [19] [11] 4,135,048
Marquez [45] Jan. 16, 1979

[54] ANAPHYLACTIC INHIBITING TRANS-OCTAHYDRONAPHTO[1,2-c:5,6-c'] DIPYRAZOLES

[75] Inventor: Victor E. Marquez, Caracas, Venezuela

[73] Assignee: Laboratorios Cosmos S.A., Caracas, Venezuela

[21] Appl. No.: 797,870

[22] Filed: May 17, 1977

[51] Int. Cl.$^2$ ............................................. C07D 231/56
[52] U.S. Cl. ................................ 548/369; 560/119; 260/464; 260/586 F; 424/273 P
[58] Field of Search .......................... 562/501; 548/369
[56] References Cited
U.S. PATENT DOCUMENTS 3,842,088 10/1974 Hakeck et al. ..................... 548/369
3,926,988 12/1975 Krapcho et al. ..................... 548/369

OTHER PUBLICATIONS

Vesely et al., CA, vol. 30:4496 (1936).
Vesely et al., CA, vol. 32:5830 (1938).

Primary Examiner—Natalie Trousof
Assistant Examiner—Natalia Harkaway
Attorney, Agent, or Firm—Holman & Stern

[57] ABSTRACT

Compounds for use as orally active anaphylactic inhibitors are disclosed. The compounds are trans-2,3b,4,5,7,8b,9,10-octahydronaphto[1,2-c:5,6-c'] dipyrazoles which may be substituted in both of the pyrazole rings. Also disclosed are intermediate compounds which are the corresponding trans-2,6-bis (hydroxymethylene) decalin-1,5-diones.

2 Claims, No Drawings

ANAPHYLACTIC INHIBITING TRANS-OCTAHYDRONAPHTO[1,2-C:5,6-C′] DIPYRAZOLES

BACKGROUND AND SUMMARY OF THE INVENTION

The known compound, cromolyn sodium (sodium cromoglycate, SCG) has the property that it inhibits the release of allergic mediators from sensitized tissues but does not interfere with the combination of antigen and antibody. However, this prior art compound has the disadvantage that it has been found to lack oral activity.

The present invention relates to new heterocyclic nitrogen compounds that are useful as pharmacological agents and to methods of their synthesis. More particularly, the compounds of the present invention are trans-2,3b,4,5,7,8b,9,10-octahydronaphto [1,2-c:5,6-c′]dipyrazoles which may be substituted in both of the pyrazole rings. The compounds of the present invention are useful as orally active anaphylactic inhibitors for the treatment of asthmatic symptoms.

The compounds which are the subject of the present invention are represented by the formula:

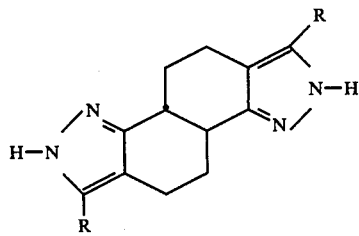

wherein R is H, OH, CN, $CO_2Me$, $CO_2Et$, $CO_2H$, $CF_3$, halogen, $NO_2$, or $NH_2$. These groups in general tend to increase or enhance the hydrogen-bonding capacity of the pyrazole hydrogen, a fact that is related to the biological properties of these molecules. In fact, removal of the pyrazole hydrogen by appropriate substitution eliminates completely the biological activity.

The octahydronaphto[1,2-c:5,6-c′]dipyrazoles of the present invention wherein R is H, OH, CN, $CO_2Et$, $CO_2Me$, $CO_2H$ or $CF_3$ may be produced by reacting the corresponding trans-2,6-bis(hydroxymethylene)decalin-1,5-dione of the formula:

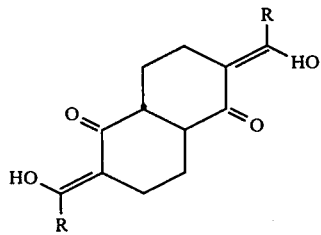

wherein R is as above defined, with more than two equivalents of hydrazine in refluxing ethanol for 6 hrs.

In the case of the present compounds wherein R is halogen or $NO_2$, these groups are introduced after formation of the parent compound of formula (1), (R = H) by appropriate substitution. Once the $NO_2$ analog is obtained, the amino ($NH_2$) compound will also be obtainable by catalytic reduction.

The starting materials designated in formula (2) herein are also considered novel and can be obtained from known trans-decalin-1,5-dione by reaction under nitrogen with an excess of the corresponding ester of the formula:

$$R-CO_2R' \qquad (3)$$

wherein R is equal to H, OMe, OEt, CN, $CO_2Me$, $CO_2Et$, or $CF_3$ and R′ is Me or Et, in the presence of sodium methoxide as catalyst and dry pyridine as solvent. The known trans-decalin-1,5-dione may be obtained by starting with commercially available 1,5-decalindiol which is subjected to oxidation under the conditions reported by W. S. Johnson et al. *J. Amer. Chem. Soc.,* 73,5464 (1951). As reported by these authors, the resulting dione is equilibrated to its most stable trans isomer and obtained as pure trans-decalin-1,5-dione.

DESCRIPTION OF THE PREFERRED EMBODIMENTS

The following Examples I and II describe methods of preparation of compounds having formulas (1) and (2) as shown above. Melting points were determined by means of an Electrothermal capillary melting point apparatus and they are uncorrected. A Perkin-Elmer Model 727 infrared spectrophotometer was employed for ir spectra, using either nujol mulls or chloroform solutions. A Varian Associates Model EM-360 analytical nmr spectrometer was used for nmr spectra. Ultraviolet spectra were recorded on a Beckman Model 25 spectrophotometer, utilizing 1 cm path cells. Mass spectra were obtained in a Hitachi Perkin-Elmer RMU-6H instrument at 70 eV.

EXAMPLE I

Example of a compound of formula (2) wherein R = H.
trans-2,6-Bis(hydroxymethylene)decalin-1,5-dione. A mixture of 1.66 g (10 mmole) of trans-decalin-1,5-dione, 2.16 g (40 mmole) of $NaOCH_3$, 9.2 ml (130 mmole) of ethyl formate, and 70 ml of dry pyridine was stirred under nitrogen at room temperature for 21 hr. After the mixture was adjusted to a pH between 5 and 6 with the aid of 51 ml of AcOH and 471 ml of water, it was extracted with benzene several times. The benzene layers were thoroughly washed with water and then were extracted with 2% KOH solution. The basic extracts were washed with ether and then after reacidification with AcOH they were thoroughly extracted again with benzene. The benzene extracts were dried ($Na_2SO_4$) and then were reduced to dryness to give 2 g (90%) of crude product. Recrystallization from ethanol afforded trans-2,6-Bis(hydroxymethylene)decalin-1,5-dione as a fine yellow powder, mp 155°–157°; ir (nujol) 1640 and 1570 cm$^{-1}$; nmr ($CDCl_3$)δ2.3 (broad multiplet, 10), 9.00 (s,2), and 14.50 (s,2); mass spectrum m/e 222($M^+$.).

Anal. Calcd. for $C_{12}H_{14}O_4$: C, 64.85; H, 6.35. Found: C, 64.69, H, 6.38.

EXAMPLE II

Example of a compound of formula (1) wherein R = H.
trans-2,3b,4,5,7,8b,9,10-Octahydronaphto[1,2-c:5,6-c′]dipyrazole. A mixture of 1.11 g (5 mmole) of trans-2,6-Bis(hydroxymethylene) decaline-1,5-dione, 1 ml (c.a. 0.02 mole) of hydrazine hydrate and 50 ml of ethanol was refluxed for 6 hr. After the total volume was reduced to about half, the compound slowly precipitated at room temperature. The solid was collected, dried and recrystallized twice from ethanol to yield 0.7 g (65%) of trans-2,3b,4,5,7,8b,9,10-Octahydronaphto[1,2-c:5,6-c']dipyrazole as very fine off-white crystals, mp 300° dec; ir (nujol) 3200 (s, broad), 1600 (w), 1580 (w), 1340 (m), 1180 (m), 1100 (m), 1080 (m) 980 (s), 880 (m), and 820 (m); nmr (DMSO-$d_6$)$\delta$7.40 and 7.30 (singlets, 2), and 12.6 (broad singlet, 2); mass spectrum m/e 214 (M$^+$.).

Anal. Calcd for $C_{12}H_{14}N_4$: C, 67.26; H, 6.59; N, 26.15; Found: C, 67.09; H, 6.48; N, 26.10.

BIOLOGICAL ACTIVITY

The compound of formula (1), R = H, has been tested extensively. The tests performed for PCA (Passive Cutaneous Anaphylaxis) are rather simple and many references in the literature can be found as, for example, in J. Goose and A. M. J. N. Blair, *Immunology*, 16, 749 (1969). The method basically includes injecting rats intracutaneously on their shaved backs with sera (0.5 ml) from rats immunized with egg albumin and Bordetella pertusis vaccine. After the initial injections (24 hr) test drugs are administered p.o. at a dose of 100 mg/kg. One hour later, 1 ml of 0.5% solution of Evans Blue dye and 8 mg of egg albumin are injected iv. After an additional 140 minutes the animals are sacrificed, the skin on their backs is turned back, and the wheal sizes are measured. Reduction of the wheal size of the treated animals is expressed as a percent inhibition in relation to the control group which receives no drug. The results of the use of the compound of formula (1), R = H, compared to those obtained with sodium cromoglycate (SCG) are shown in Table I.

TABLE I

| Compound | Route of Administration | Dose | Biological Activity | Remarks |
|---|---|---|---|---|
| Formula (1), R = H | P.O. | 100 mg/kg | 67 | |
| Formula (1), R = H | P.O. | 50 mg/kg | 54 | approx. MED |
| Formula (1), R = H | P.O. | 25 mg/kg | 40 | |
| SCG[a] | I.P. | 60 mg/kg | 60 | |

TABLE I-continued

| Compound | Route of Administration | Dose | Biological Activity | Remarks |
|---|---|---|---|---|
| SCG | I.V. | 5 mg/kg | 75 | ED 100 |

[a]SCG = Sodium Cromoglycate

Systemic anaphylaxis was also prevented at 50 mg/kg in mice one hour after oral administration indicating that the compound is not specific for reaginic antibody reactions and yet no conventional antihistaminic or antiserotonin activity was detected in vitro at a dose of 10 mcg/ml. The results comparing the activity of the compound of formula (1), R = H, against that of phenyltoxolamine are summarized in Table II.

TABLE II

| Compound | Route of Administration | Dose | Biological[b] Activity | Remarks |
|---|---|---|---|---|
| Phenyltoxolamine | P.O. | 50 mg/kg | 0 | ED 100 |
| Formula (1), R = H | P.O. | 50 mg/kg | 0 | MED |
| Formula (1), R = H | P.O. | 25 mg/kg | 1 | |

[b]Critical biological response = 0 (less than ½ of the mice exhibit anaphylaxis after one hour).

It is thought that the invention and many of its attendant advantages will be understood from the foregoing description, and it will be apparent that various changes may be made in the invention as described herein without departing from the spirit and scope of the invention or sacrificing its material advantages, the forms hereinbefore described being merely preferred embodiments thereof.

It is claimed:

1. A compound of the formula

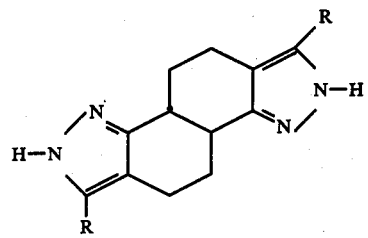

wherein R is H, OH, CN, $CO_2Me$, $CO_2Et$, $CO_2H$, $CF_3$, halogen, $NO_2$ or $NH_2$.

2. The compound of claim 1 wherein R is H.

* * * * *